(12) United States Patent
Jun et al.

(10) Patent No.: US 9,021,881 B2
(45) Date of Patent: May 5, 2015

(54) PROBING SYSTEM FOR MEASUREMENT OF MICRO-SCALE OBJECTS

(71) Applicant: UVic Industry Partnerships Inc., Victoria (CA)

(72) Inventors: Martin B. G. Jun, Victoria (CA); Chan-Seo Goo, Victoria (CA)

(73) Assignee: UVic Industry Partnerships Inc., Victoria, CA (US)

( * ) Notice: Subject to any disclaimer, the term of this patent is extended or adjusted under 35 U.S.C. 154(b) by 365 days.

(21) Appl. No.: 13/711,591

(22) Filed: Dec. 11, 2012

(65) Prior Publication Data

US 2013/0145848 A1 Jun. 13, 2013

Related U.S. Application Data

(60) Provisional application No. 61/569,710, filed on Dec. 12, 2011.

(51) Int. Cl.
| | |
|---|---|
| *G01B 17/06* | (2006.01) |
| *G01N 29/14* | (2006.01) |
| *G01B 5/012* | (2006.01) |
| *G01N 29/265* | (2006.01) |

(52) U.S. Cl.
CPC ............... *G01N 29/14* (2013.01); *G01B 17/06* (2013.01); *G01B 5/012* (2013.01); *G01N 29/265* (2013.01)

(58) Field of Classification Search
CPC ....................................................... G01B 17/06
USPC ...................... 73/587; 33/503, 558
See application file for complete search history.

(56) References Cited

U.S. PATENT DOCUMENTS

2007/0196190 A1 8/2007 Bourne et al.

FOREIGN PATENT DOCUMENTS

CA 2571275 6/2007

OTHER PUBLICATIONS

Bourne et al., "An acoustic emission-based method for determining contact between a tool and workpiece at the microscale," *ASME Transactions, Journal of Manufacturing Science and Engineering*, vol. 130, pp. 031101-1-031101-8 (Jun. 2008).
Carl Zeiss, "F25 Measuring Nanometers," *Microsystem & Optical CMMs*, http://www.zeiss.com/f25 (Mar. 20, 2011).
Dai et al., "A high precision micro/nano CMM using piezoresistive tactile probes," *Journal of Measurement Science and Technology*, vol. 20, pp. 084001-1-084001-9 (Jun. 2009).
Fan et al., "Study of a noncontact type micro-CMM with arch-bridge and nanopositioning stages," *Journal of Robitics and Computer-Integrated Manufacturing*, vol. 23, pp. 276-284 (2007).
Kung et al., "Ultrapresision micro-CMM using a low force 3D touch probe," *Journal of Measurement Science and Technology*, vol. 18, pp. 319-327 (Jan. 2007).

(Continued)

*Primary Examiner* — John Chapman, Jr.
(74) *Attorney, Agent, or Firm* — Klarquist Sparkman, LLP

(57) ABSTRACT

An apparatus for measuring dimensions of a micro-scale object includes a movable stylus, a probe and at least one acoustic emissions sensor. The movable stylus is positionable to contact an object to be measured. The probe is rotatably coupled to the stylus and has a distal end that circumscribes a circle when rotated. The acoustic emissions sensor is operatively coupled to the probe. The sensor is operative to detect acoustic emissions generated from contact between the distal end of the probe and the object, thereby allowing dimensions of the object to be determined.

20 Claims, 15 Drawing Sheets

(56) References Cited

OTHER PUBLICATIONS

Muravin, "Acoustic emission science and technology," *Journal of Building and Infrastructure Engineering of IAEA* (2009).

Pril, "Development of high precision mechanical probe for coordinate measuring machines," *PhD Thesis, Technische Universiteit Eindhoven* (2002).

Schwenke et al., "Opto-tactile Sensor for 2D and 3D measurement of small structures on coordinate measuring machines," *Technisches Messen*, vol. 66, pp. 485-489 (1999).

Stoyanov et al., "Modelling and prototyping the conceptual design of 3D CMM microprobe," $2^{nd}$ *Electronics System Integration Technology Conference*, Greenwich, UK, IEEE, 978-1-4244-2814, pp. 193-198 (Apr. 2008).

Takamasu et al., "Development of pneumatic ball probe for measuring small hole," *Proc. Int. Conf. on Precision Engineering, (ICPE '97)*, vol. 2, pp. 767-771 (1997).

Takaya et al., "Fundamental study on the new probe technique for the nano-CMM based on the laser trapping and Mirau interferometer," *Measurement*, vol. 25, pp. 9-18 (1999).

Weckenmann et al., "Probing Systems in Dimensional Metrology," *Ann. CIRP*, vol. 53, pp. 657-684 (2004).

PROBING SYSTEM FOR MEASUREMENT OF MICRO-SCALE OBJECTS

CROSS REFERENCE TO RELATED APPLICATION

This patent application claims the benefit of U.S. Provisional Patent Application No. 61/569,710, filed Dec. 12, 2011, the entirety of which is hereby incorporated herein by reference.

FIELD

The subject matter of this application relates to coordinate measuring machine (CMM) or probing system, and more particularly a tactile CMM for determining three-dimensional measurements and surface profile of micro-scale solid objects and micro-scale features on bulk solid objects.

BACKGROUND

The production of micro-scale objects or components is growing in various industries. For example, biomedical devices such as catheters and biosensors are fabricated and packed with many miniature features to increase their capabilities to diagnose and treat diseases. In electronics industry, micro-electromechanical system (MEMS) devices are fabricated and incorporated with micro-scale features to enable the electronic, mechanical and electrical functionalities of those devices. In the aerospace industry, miniature components are produced and machined to precise dimensions and close tolerances to serve certain special purposes such as structural reinforcement and safety compliance. This growing need for the production of miniature components or micro-scale objects requires suitable metrology tools and systems, such as a coordinate measuring machine (CMM) or a probing system, to provide quality control mechanism for ensuring conformance of dimensions and surface profile with target specifications.

Generally, dimensional measurements and surface profiles of objects are determined by sensing or probing the surface using a probe through a non-contact or a contact method. The use of an optical probe or a laser probe provides a non-contact means to sense and scan the surface of an object. An example of laser-based method is shown in U.S. Pat. No. 4,7333,969, which describes a laser-based sensor system that can function as a CMM probe. While it provides a non-contact method, the optical or laser-based method is typically costly due to the use of expensive optics or laser system and the bulky structure required to house the whole system. Additionally, objects with intricate surface profile, such as those involving deep holes and complex curvatures, present a significant challenge to optical or laser-based method because those surface features can act as barriers that make the probe optically blind to some areas of interest.

On the other hand, the use of a tactile probe provides a contact method where measurements are determined when the probe establishes a physical contact with the surface of the object. An example of a tactile method and device is shown in U.S. Pat. No. 7,752,766. Typical design of a tactile probe involves a ball, such as a ruby or a steel sphere, as a probe tip that is attached to one end of the stylus. To improve the accuracy of measurements especially when conducting measurements in the micro-scale, the tactile probe needs to be fabricated to smaller sizes. Down-scaling the tactile probe usually leads to complex detection algorithms and a costly metrology tool. The finer the probe tip becomes, the higher is its fabrication cost. Also as the size of the tactile probe decreases, the probe becomes more susceptible to the "snap-in" effect. The "snap-in" effect occurs when the probe approaches within micrometers to the surface of the object, and is manifested by the sudden bending and adhesion of the probe to the surface of the object. This "snap-in" effect can introduce measurement errors and even damage the tactile probe. Likewise, frequent replacement of tactile probe from normal wear and tear or accidental damage can be costly.

Therefore, it is desirable to develop a micro-scale metrology tool, particularly a CMM or probing system, that is cost-effective and capable to provide precise measurements in the micro-scale. The CMM or probing system should be able to determine the precise spatial coordinates of multiple points along the contour of micro-scale solid objects and micro-scale features on bulk solid objects. By processing the recorded spatial coordinates using applicable mathematical algorithms, the dimensions, surface profile and construction of objects can be determined accurately.

SUMMARY

Described below are various approaches to providing a cost-effective apparatus and method for determining precise three-dimensional measurements and surface profiles of micro-scale solid objects and micro-scale features on bulk solid objects. These approaches can be used in various metrology applications including dimensional inspection of components, determination of geometrical construction of objects, and surface characterization.

In one implementation, an apparatus for measuring dimensions of a micro-scale object comprises a movable stylus, a probe and at least one acoustic emissions sensor. The movable stylus is positionable to contact an object to be measured. The probe is rotatably coupled to the stylus and has a distal end that circumscribes a circle when rotated. The acoustic emissions sensor is operatively coupled to the probe. The sensor is operative to detect acoustic emissions generated from contact between the distal end of the probe and the object, thereby allowing dimensions of the object to be determined.

The probe can comprise an angled element that is angled with respect to an axis of rotation extending through a proximal end of the probe where the probe is joined to the stylus. The probe's path in rotation can define a cone shape.

The apparatus can comprise a platform upon which the object can be positioned. The acoustic emissions sensor can be connected to the platform.

The apparatus can comprise a circuit that includes the acoustic emissions sensor and a processor. The processor is operable to process the acoustic emissions data received from the acoustic emissions sensor and to subject the acoustic emissions data to an algorithm to determine coordinates in space at points of contact along the object.

The apparatus can comprise a display operable to display data to a user during operation of the apparatus.

The probe can comprise a bent wire. The probe can comprise an angled element having a proximal end positioned at an axis of rotation and a distal end spaced apart from the axis of rotation. In some implementations, the angle between the axis of rotation and the angled element can be between about 30 degrees and about 60 degrees, although an angle between 0 and 90 degrees can be used. In some implementations, the probe has a length of at least 1 mm.

According to one method implementation, dimensions of a micro-scale object are measured by positioning a movable probe near an object to be measured, causing a distal end of the probe to rotate, detecting acoustic emissions and, if detected acoustic emissions indicate that the distal end of the probe is in contact with the object, then pausing movement of the probe and determining a coordinate corresponding to the contact between the probe and the object.

The method can include determining if the detected acoustic emissions exceed a threshold. If the acoustic emissions do not exceed a threshold, then rotation of the probe can be continued without pausing.

Detecting acoustic emissions can include detecting acoustic emissions with an acoustic emissions sensor operatively coupled to the probe. Causing a distal end of the probe to rotate can include causing rotation at about 30,000 rpm to about 60,000 rpm. The probe can be configured to circumscribe a circle of about 200 µm to about 700 µm.

The method can comprise resuming rotation of the probe following determination of the coordinate. In addition, the method can comprise using a computing device programmed with different algorithms for determining a coordinate depending upon the probe's direction of approach toward the object.

The method can comprise determining a profile of the object from multiple contact points.

The method can comprise setting an approach speed of the probe towards the object to increase accuracy of measurement. Similarly, the method can comprise setting a probing force that the probe exerts upon contact with the object to increase accuracy of measurement.

The foregoing and other objects, features, and advantages will become more apparent from the following detailed description, which proceeds with reference to the accompanying figures.

BRIEF DESCRIPTION OF THE DRAWINGS

The following figures set forth different aspects and embodiments and serve to explain the principles, operation and performance of the apparatus and methods.

FIG. 4A is a schematic diagram of an event of no contact between the rotating wire-based probe and the surface of the object, while

FIG. 5A is a schematic diagram of an event of physical contact between the rotating wire-based probe and the surface of the object, while

FIG. 10(a) is a schematic diagram of an ideal touch or physical contact between the tactile probe and the surface of an object wherein an allowable stylus deflection ($W_a$) is shown, while FIG. 10(b) is a schematic diagram that shows an event of collision between the stylus and the surface of an object.

FIG. 20A is graphical illustration showing the effect of bend angle of the probe wire on repeatability, while

DETAILED DESCRIPTION

In general, described below is an apparatus and method for determining precise three-dimensional measurements of an object 5 using acoustic emissions generated by the physical contact between a probe in the form of a rotating bent wire (angled element) and the surface of the object. According to the described approach, a relatively small probe is used, which maintains the device's precision, and the probe is rotated, which allows discerning contact by detecting acoustic emissions with a remotely positioned sensor or transducer. Because the rotating probe circumscribes a circle much larger than the dimension of its distal end, there is the advantage that imbalance due to the mass of its distal end is minimal. The length of its distal end can be controlled easily, leading to easy control of circumscribed circle by its distal end. Wear of its distal end does not require disposal of the probe; rather, the circumscribed circle diameter by the worn distal end can be easily measured and calibrated against a calibration artifact. With the described apparatus and methods, measuring of micro-scale objects can be carried out in a cost-effective, robust and accurate fashion.

More particularly, the object 5 is either a solid micro-scale object or a micro-scale feature on a solid bulk object. Example of a micro-scale feature is a tiny deep hole present in a biomedical catheter. Moreover, the apparatus functions as a CMM or probing system that determines the precise spatial coordinates of multiple points along the contour or surface of a solid object 5.

Figure 1:
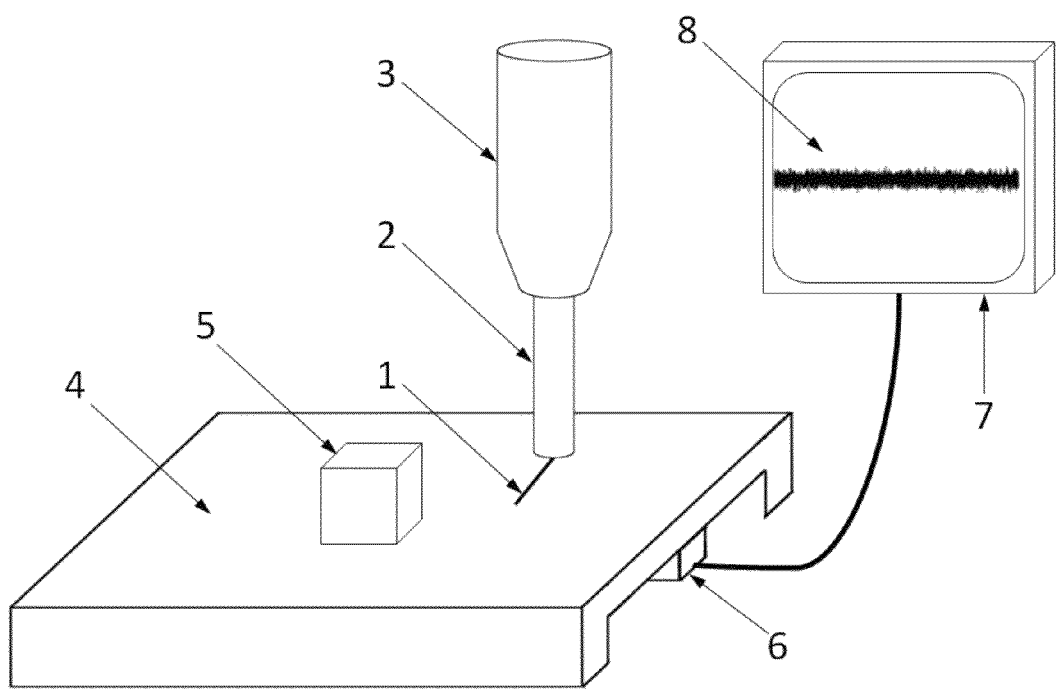
FIG. 1 is a schematic diagram of the apparatus and method of the present invention, wherein a CMM or probing system that uses a wire-based probe design and works based on acoustic emission sensing mechanism is provided.

The apparatus comprises of a bent wire as the wire-based probe 1, a stylus 2, a spindle 3, a platform stage 4, at least one acoustic emission sensor 6, and a computing device 7 (see FIG. 1). One end of the bent wire is attached to one end of the stylus 2. The other end of the stylus 2 is attached to a spindle 3 that is capable of making multiple revolutions per minute. The at least one acoustic emission sensor 6 is attached to a platform stage 4 where an object 5 for measurement resides. Alternatively, the acoustic sensor 6 can be positioned at any other known location, either fixed or movable within an operable detecting range of the probe 1. The whole assembly of the bent wire as the wire-based probe 1, the stylus 2 and the spindle 3 are collectively being directed towards the surface of the object 5 on the platform stage 4 when gathering measurements on the object 5 under study.

In one embodiment, there is a bent wire that functions as a tactile wire-based probe 1 of a CMM. The bent wire can be made of tough material such as certain metals, alloys and composites. The bent wire may also contain special coatings to inhibit wear and tear and to improve its interaction with the surface of an object 5. Additionally, the bent wire may be fabricated such that its bend angle (see $\alpha_p$ in FIG. 6) may be anywhere from 0 to 90 degrees.

Figure 2:
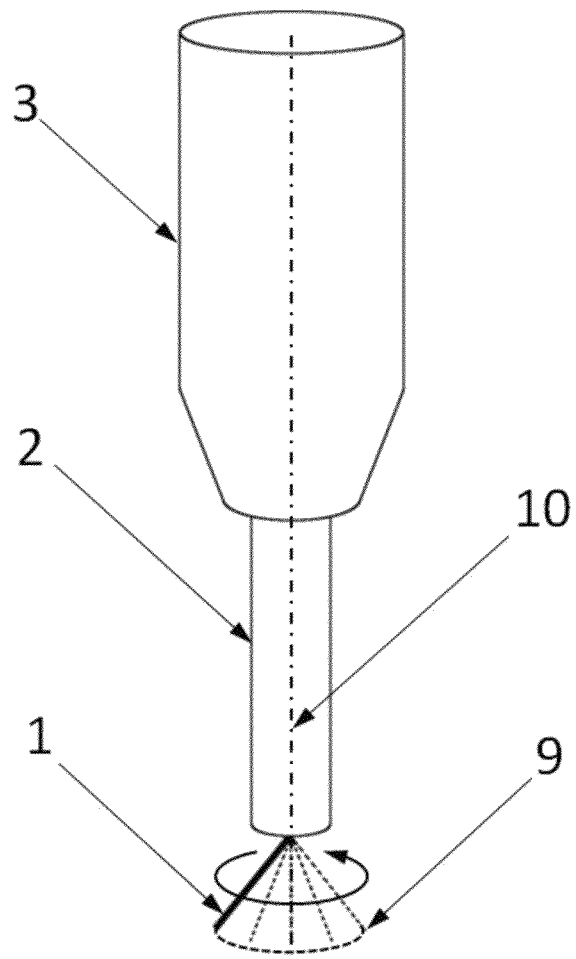
FIG. 2 is a schematic diagram of the probe assembly comprising of a spindle, a stylus and a bent wire that functions as a tactile probe, and wherein a cone-shaped probe tip is created when the said bent wire is rotated on one end about the central axis of the stylus.
Figure 3:
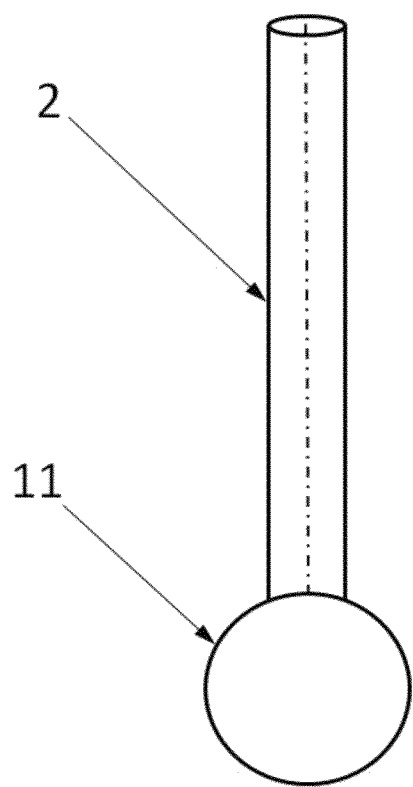
FIG. 3 is a schematic diagram of the conventional tactile probe based on ball-type probe tip design.

Furthermore, the tactile probe has notable differences in the construction and operation with respect to the tactile probe used in a conventional CMM. Typically, a conventional CMM uses a tactile probe with a ball-type probe tip 11, usually made of ruby or steel, to probe or detect the surface of an object (see FIG. 3). On the other hand, the disclosed apparatus uses a rotating bent wire to probe or detect the surface of an object (see FIG. 2). The bent wire is rotated from one of its ends about the central axis 10 of the stylus using a spindle 4 whose revolution can be controlled. As the bent wire rotates, a cone-shaped probe tip 9 is created (see FIG. 2), and its circular base has a diameter that is referred to as the "effective diameter" in this disclosure. This rotational motion-induced cone-shaped probe tip 9 is analogous to the ball-type probe tip 11 of conventional tactile CMM. By replacing the conventional ball-based probe design with a wire-based probe design, the cost of manufacturing a tactile CMM can be reduced significantly.

In another embodiment, there is a platform stage 4 that is mechanically robust to contain both the object under study and the acoustic emission sensor. The platform stage 4 may be constructed either as a fixed rigid structure or as a movable structure whose axial and rotational movements can be controlled. A movable platform stage 4 is beneficial on applications wherein the object under study is preferred to be moved around the stationary tactile probe when conducting measurements. The movable platform stage 4 may be driven by at least one motor with precision motion control to cause the platform stage 4 to move along, tilt and rotate about the three axes (X, Y and Z).

In yet another embodiment, there is a probe assembly (see FIG. 2) comprising of a wire-based probe 1, a stylus 2 and a spindle 3, wherein the probe assembly may be constructed either as a fixed rigid structure or as a movable structure whose axial and rotational movements can be controlled. A movable probe assembly is beneficial on applications wherein the object under study is preferred to be stationary relative to the probe when conducting measurements. The movable probe assembly may be driven by at least one motor with precision motion control to cause the probe assembly to move along, tilt, and rotate about the three axes (X, Y and Z).

Figure 4A:
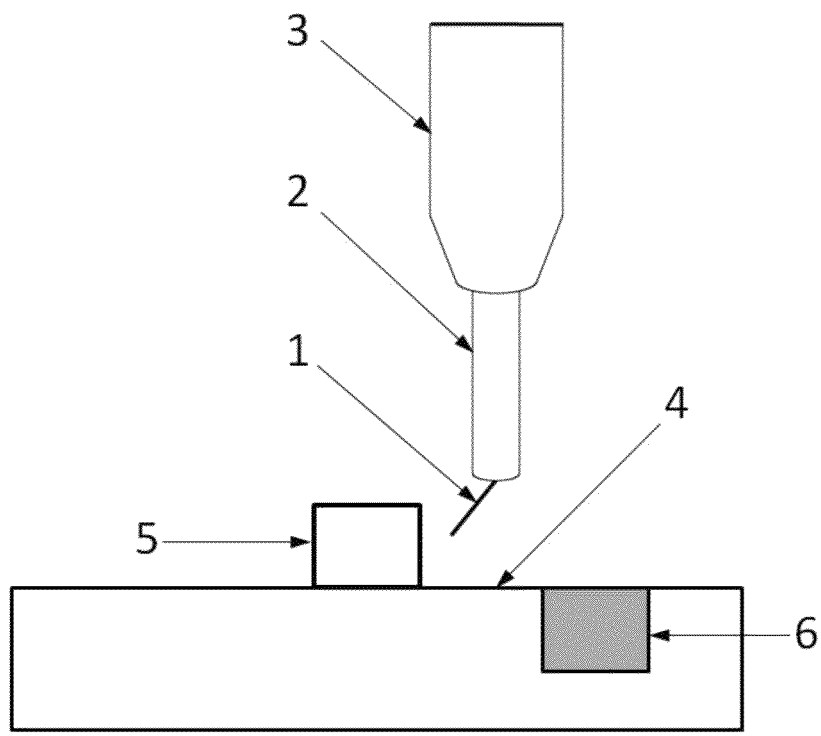
Figure 4B:
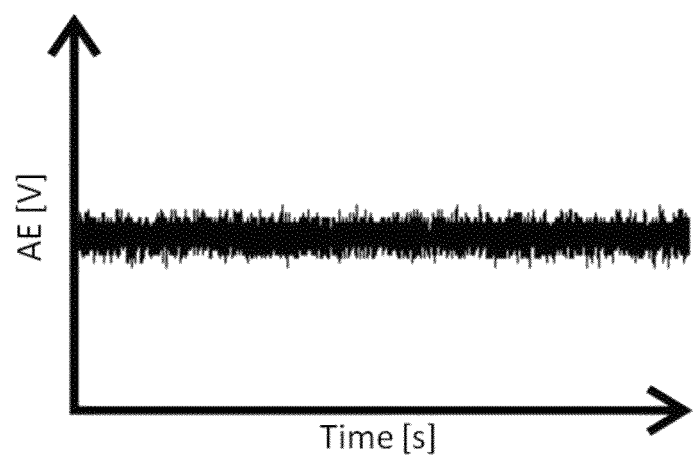
FIG. 4B is a graphical illustration of the AE signal waveform that corresponds to the event of no contact.
Figure 5A:
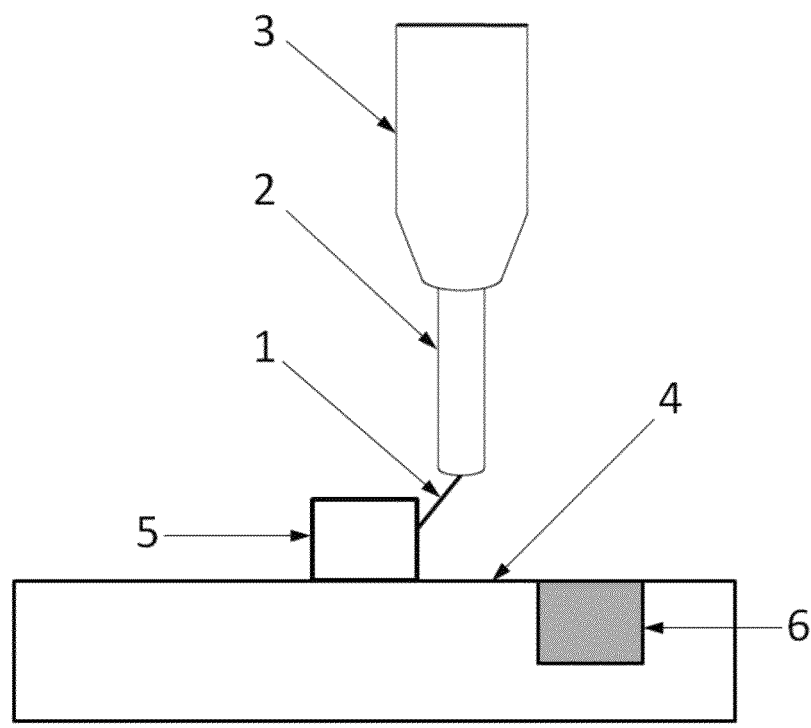
Figure 5B:
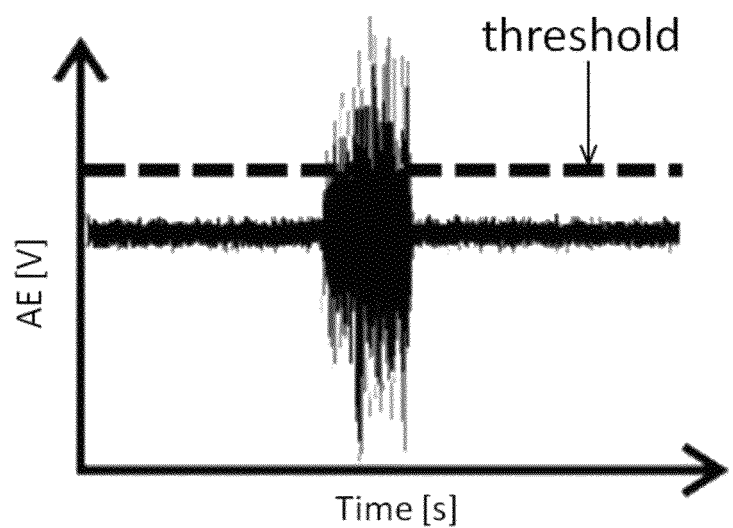
FIG. 5B is a graphical illustration of the AE signal waveform that corresponds to the event of physical contact.

In yet another embodiment, there is at least one acoustic emission sensor 6 that receives AE signals and subsequently transmits the AE signals to a computing device 7 where waveform signal processing is performed. The waveform of the AE signals may be shown on a display 8 of the computing device 7 for visual analysis and reference purposes. Further, the waveform of the AE signals is analyzed and processed using suitable algorithm in order to discriminate between a valid physical contact event (see FIG. 5) and a non-contact event (see FIG. 4). The algorithm uses a defined threshold for the AE signal to indicate a valid physical contact between the wire-based probe 1 and the surface of the object 5 before recording the spatial coordinates of the point where the said valid physical contact has occurred.

In yet another embodiment, there is an AE-based method to detect the surface of an object 5 and conduct measurements on the said surface of an object 5. More particularly, the AE-based method uses the AE signals generated when a rotating wire-based probe 1 makes a physical contact with the surface of an object 5. Briefly, the AE-based method comprises of the following basic steps (see FIG. 8):

(a) A rotating wire-based probe 1 approaches and makes contact with the object 5 under study;
(b) The AE signals are detected by at least one AE sensor 6 and are subsequently transmitted to a computing device 7;
(c) The AE signals are processed and analyzed real-time by a computing device 7 using a suitable algorithm;
(d) If a threshold is met, the forward movement of the wire-based probe 1 is stopped and the coordinates of the point corresponding to the event of physical contact between the said wire-based probe 1 and the object 5 are recorded;
(e) Steps (a) to (d) are repeated on multiple points along the contour of the object 5 to determine its dimensions or geometrical characteristics.

Wire-Based Micro-Probe Geometry

Figure 6:
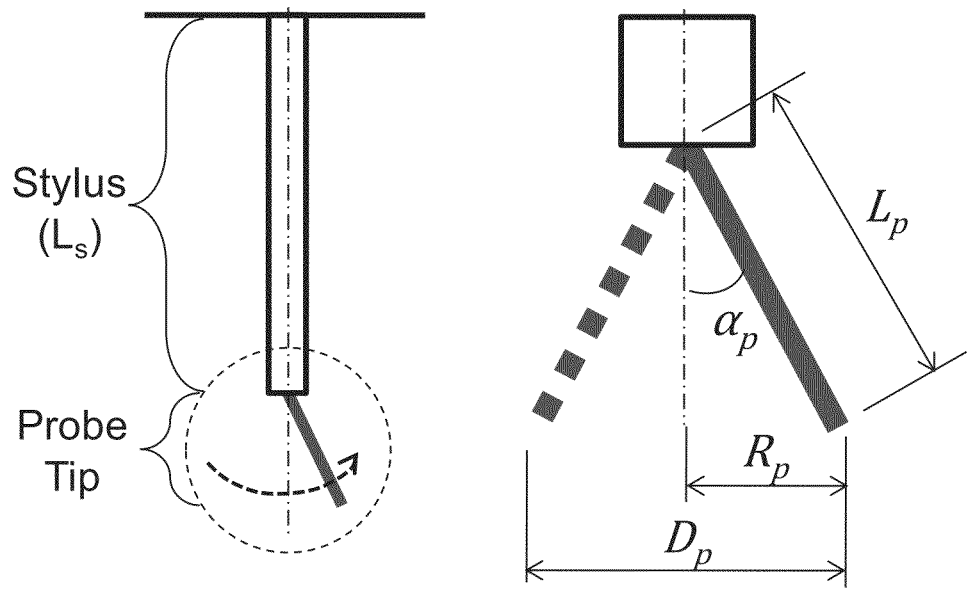
FIG. 6 provides the schematic diagrams of the structure and geometry of a micro-probe based on a rotating bent wire.

A schematic of the wire-based probe 1 is displayed in FIG. 6. An alloy steel wire with diameter of 100 μm is coupled to the end of the stylus. The wire is then bent at an angle ($\alpha_p$) such that, as the stylus rotates, the effective diameter of the probe ($D_p$) is larger than the stylus diameter ($D_s$), i.e., $D_p > D_s$. The probe effective diameter $D_p$ can be written as:

$$D_p = 2R_p = 2L_p \sin \alpha_p \tag{1}$$

Figure 7:
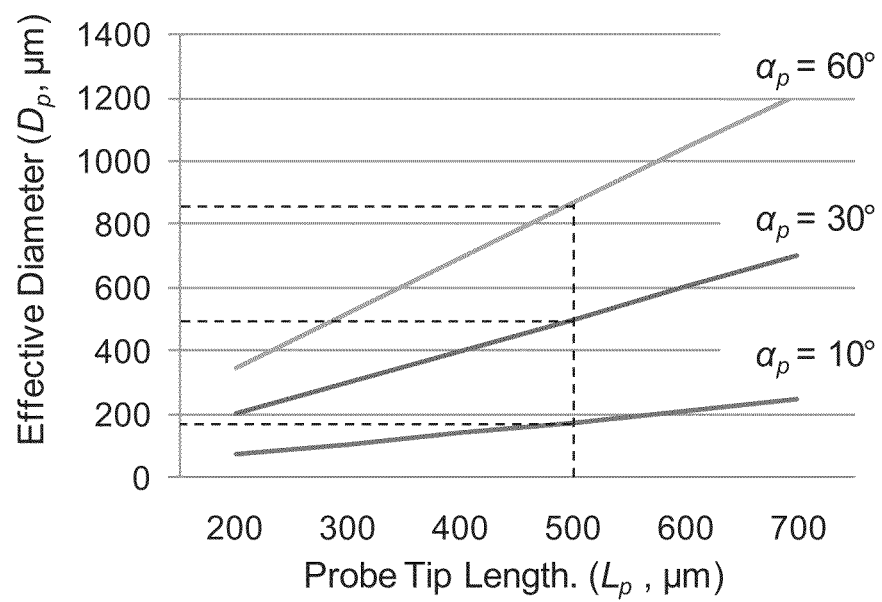
FIG. 7 is a graphical illustration showing the effects of bend angle and wire length of the wire-based probe on the effective diameter of the probe.

The effects of the bend angle ($\alpha_p$) and the wire length ($L_p$) on the "effective diameter" ($D_p$) are shown in FIG. 7. It shows that fabrication of a probe with a desired effective diameter can be achieved by adjusting the wire length and bend angle. For example, for a probe tip whose length is fixed at 500 μm, the effective probe diameter becomes 174, 500, and 866 μm at probe bend angles of 10, 30, and 60 degrees, respectively.

Acoustic Emission-Based Micro-Probe Sensing Method

Figures 8A, 8B:
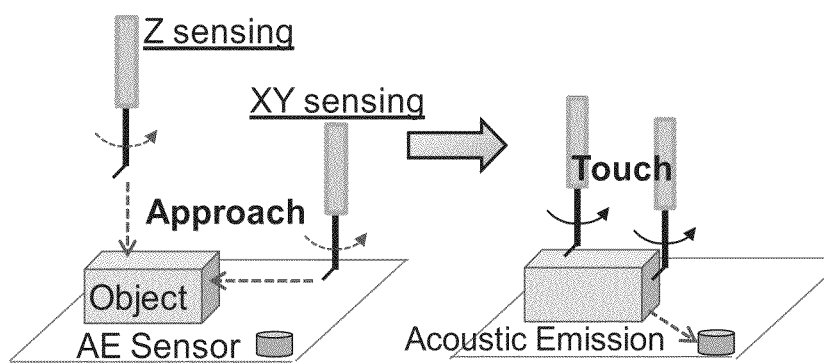
FIGS. 8(a) to 8(d) is a functional diagram that shows the series of basic steps involved in the AE-based method.
Figures 8C, 8D:
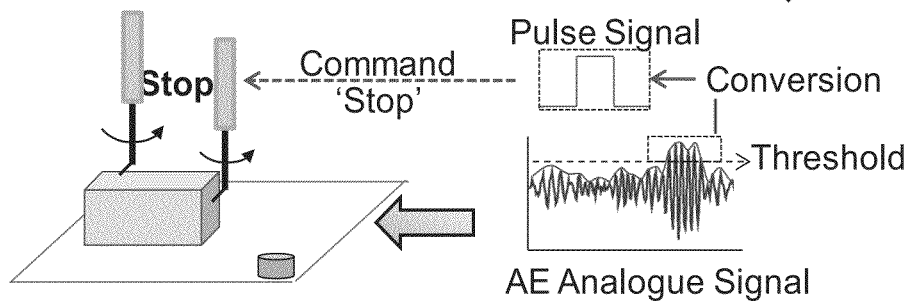

The sensing method for the micro-probe is schematically summarized in FIG. 8. The probe is rotated and commanded to approach the object at a given approaching speed (see FIG. 8a). As soon as the tip makes contact with the object surface (FIG. 8b), a burst of generated AE signal is picked up by the AE sensor as shown in FIG. 8c. The AE signal is generated due to the rubbing between rotating tip and the object surface. If the root-mean-square (RMS) value of the AE signal is larger than a threshold value, a pulse is generated to halt the probe (see FIG. 8d) and the position (i.e., spatial coordinate information) is recorded. Pulses generated due to subsequent AE generation are ignored.

The disclosed probing system may use at least one AE sensor to detect the AE signals from different directions. In the testing of the first prototype of the disclosed probing system, only one AE sensor is used to sense the touch in X, Y, and Z directions (see FIG. 8). The sensing method is slightly different in the Z direction because, when touch is detected, the wire tip is in contact with the surface for the entire revolution, whereas the wire tip is in contact with the surface for a short duration per revolution in the X and Y directions. Also, the resolution of the probing system depends on the feed rate (μm/rev) determined by the rotating speed (rev/min) and the approaching speed (mm/min). When the micro-probe is at the surface, because there is only one probe tip rotating, the touch between the probe tip and the object surface is guaranteed after a full revolution of the probe.

Figure 9:
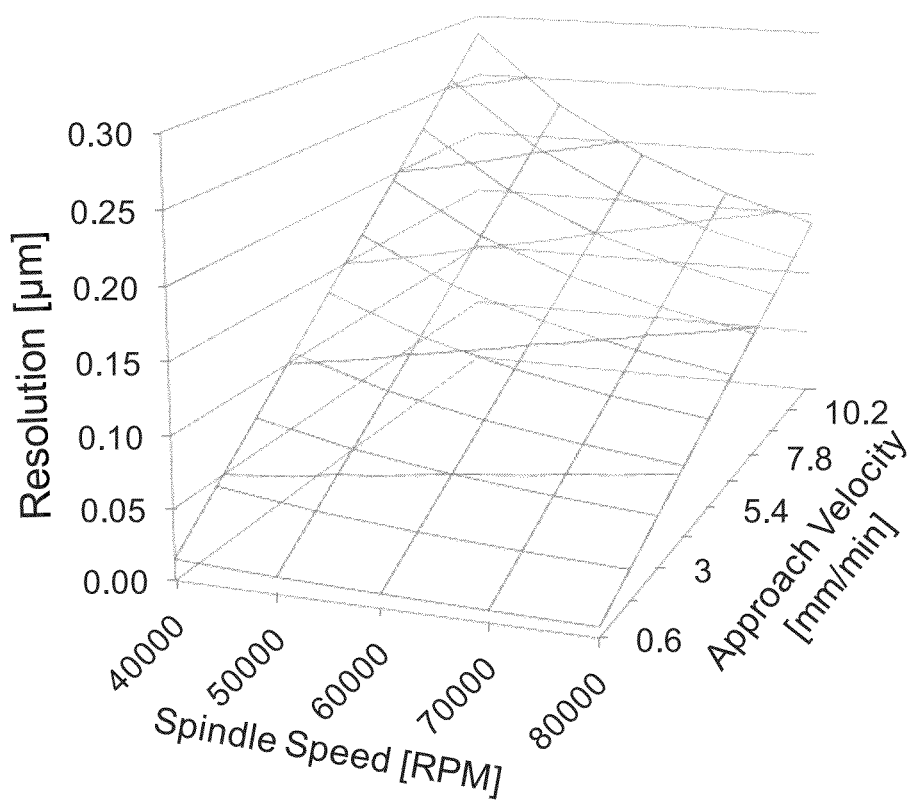
FIG. 9 is a graphical illustration that shows the effects of spindle speed and approach velocity on the resolution of the probe.

FIG. 9 shows the effects of the spindle rotational speed and the approaching speed on the resolution of the probe. Decreasing the approaching speed and increasing the rotational speed decreases the feed rate (μm/rev) and thus results in better resolution. It is shown in FIG. 9 that, for example, at 60,000 rpm and the approaching speed of 1.2 mm/min, the resolution becomes less than 0.05 μm.

Probing Force Analysis

The probing force and elastic deformation considering the probe design are discussed in this section. For conventional spherical probe tips, according to Hertz theory (Johnson, 1985), the maximum acceptable probing force, $F_p$ before plastic deformation is expressed as (Küng, 2007), $$F_p \approx 21 \frac{Y^s}{E_s^2} R_s^2 \qquad (2)$$

where $E_s$ is the equivalent Young's modulus, Y is the material yield strength, and $R_s$ is the radius of the sphere. For a probing sphere made of an alloy steel, for example, for a probing sphere with the radius of 250 μm, the acceptable contact force becomes 60 mN. Because of the parabolic relationship, as the size of the probe sphere decreases, the sensitivity of the probing system must be enhanced significantly in order to detect the touch before the contact force starts to plastically deform the sphere.

Figures 10A, 10B:
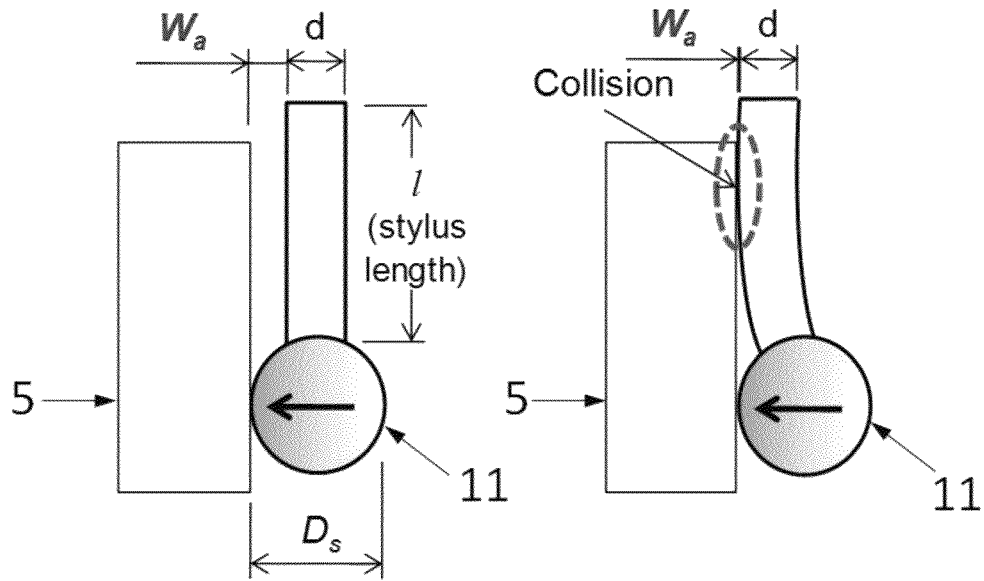

Under the maximum probing allowable force, the elastic deflection, $W_s$ of the stylus is expressed as (Weckenmann et. al., 2004), $$W_s = \frac{64 F_p l^3}{3\pi E_{st} d^4} \qquad (3)$$

where $E_{st}$ is Young's modulus of the shaft material, l and d is the length and diameter of the stylus (assumed to be cylindrical) respectively. FIG. 10 shows the schematics of the allowable stylus deflection amount, $W_a$. When the stylus deflection is larger than $W_a$, collision between the stylus and the contacting object surface occurs, causing errors in the measurement. The collision occurs when $W_s > W_a$, i.e., the stylus deflection is larger than the allowable amount.

Figure 11:
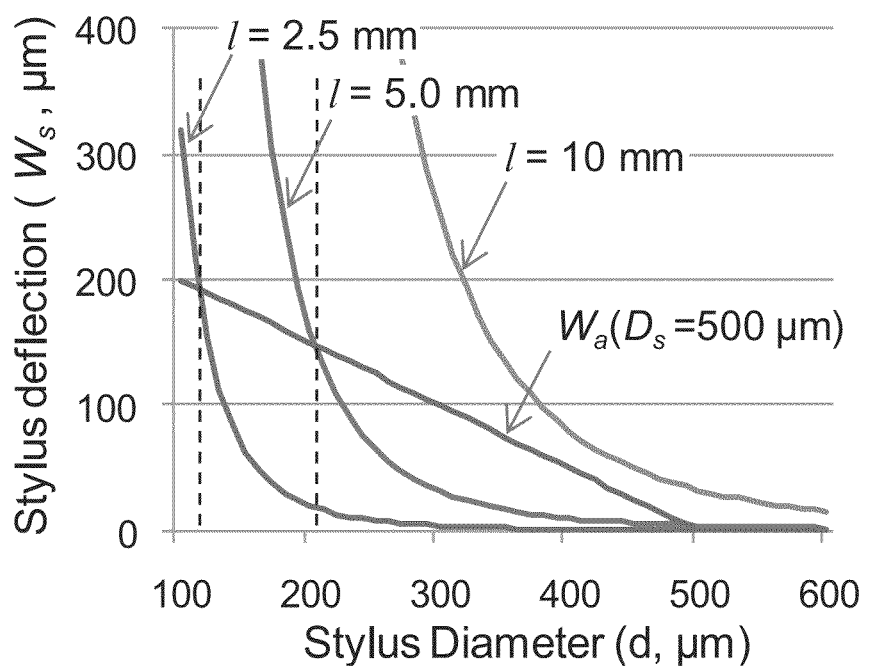
FIG. 11 is a graphical illustration that shows the stylus deflection at various configurations of stylus length and stylus diameter.

FIG. 11 shows a plot of the stylus deflection at different stylus lengths varying the stylus diameter. It also shows a plot of the allowable amount as a function of the stylus diameter. It is indicated in FIG. 11 that, for a probe sphere diameter of 500 μm, the stylus diameter cannot be smaller than 210 μm if the stylus length is 5 mm. Otherwise, collision between the stylus and the object surface would occur with the probing force, $F_p$, of 60 mN. If the stylus length is increased 10 mm, collision would always occur. This indicates that, as the spherical probe diameter is reduced, the sensitivity of touch force measurement and stiffness of the stylus need to increase significantly.

Figure 12:
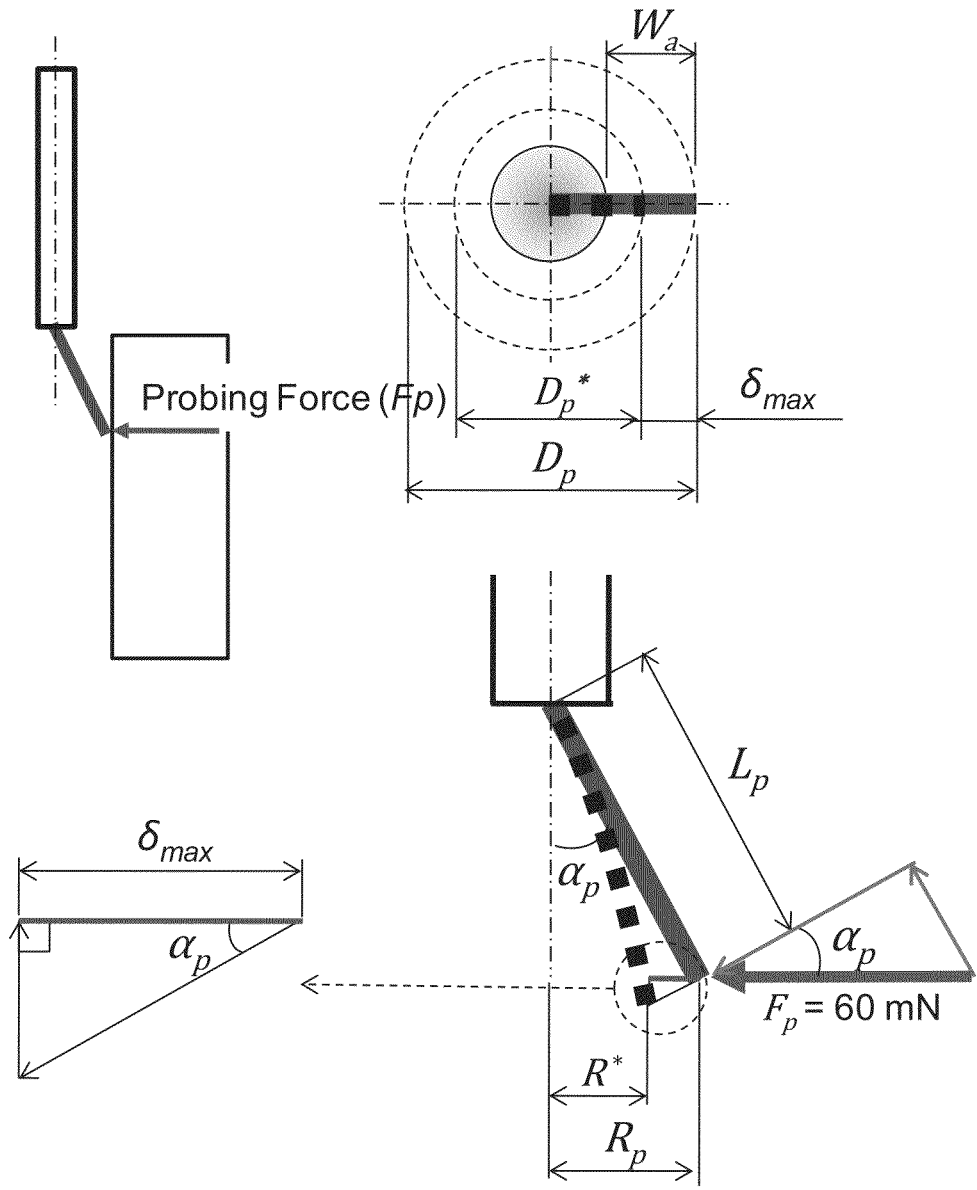
FIG. 12 provides schematic diagrams for the analysis of probe tip deflection.

For the wire-based probing system, the contact detection is not based on the measurement of contact forces but on acoustic emissions. Thus, the speed of the wire tip more likely plays more important role than the contact force for touch sensing. Nevertheless, forces are exerted on the probe tip during the contact. Since the wire diameter is much smaller than the stylus, the stylus can be considered to be rigid compared to the wire. The wire is a cantilever beam at an angle, and at the moment of contact, when the contact force is imposed on the probe tip, as shown in FIG. 12, the maximum deflection, $\delta_{max}$ in the radial direction is determined by, $$\delta_{max} = \frac{F_p L_p^3}{3 E_p I} \cos^2 \alpha_p \qquad (4)$$

where, $F_p$ is the maximum acceptable probing force, $\alpha_p$ is the probe tip bend angle, $L_p$ is the wire length, $E_p$ is the Young's Modulus of the material, and I ($=\pi r_p^4/4$, where, $r_p$ is probe radius) is Momentum of Inertia. The decrease in the effective diameter of the probe tip, $D_p^*$ due to the wire deflection can be written as $$D_p^* = D_p - 2\delta_{max}. \qquad (5)$$

Figure 13:
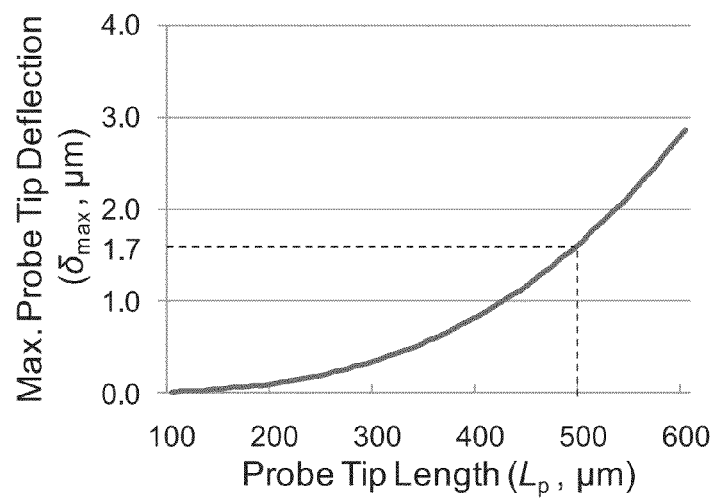
FIG. 13 is a graphical illustration of the radial deflection, $\delta_{max}$, of the wire-based probe tip at various configurations of the probe length or wire length.

When the probe tip deflection, $\delta_{max}$ is larger than the allowable stylus deflection amount, $W_a$, i.e., $\delta_{max} > W_a$, there would be collision between the stylus and the contacting object surface. For the probing force, $F_p$, of 60 mN, a thin alloy steel wire of 100 μm diameter and 500 μm length, and the probe tip bend angle of 30 degree, the deflection of the wire in the radial direction ($\delta_{max}$) comes out to be 1.7 μm as shown in FIG. 13. This indicates that as long as the wire sticks out, relative to the stylus diameter, more than 1.7 μm in the radial direction, collision would not occur with the wire-based probe under the contact force of less than 60 mN. This also implies that as the desired effective diameter of the wire-based probe is decreased, a simple analysis can be conducted to be determined the required geometry of the wire. As the effective probing diameter is decreased, fabrication of the desired geometry of the wire is relatively simpler as well, compared to spherical probes.

Experimental Setup of Contact Evaluation Experiments

Figure 14:
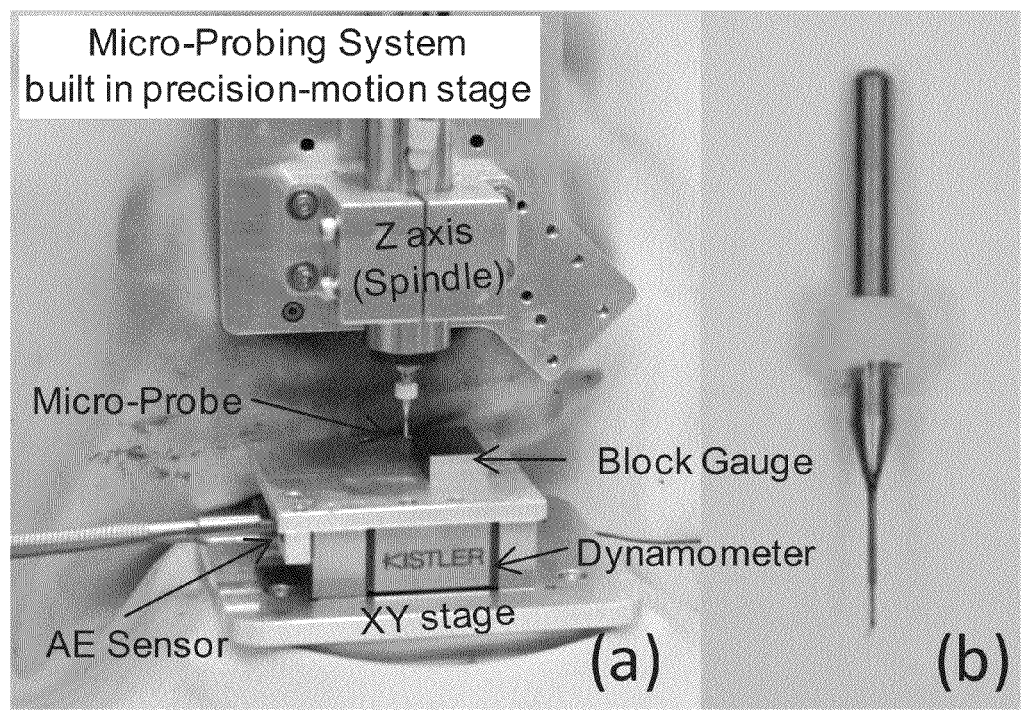
FIG. 14 is a drawing showing (a) the functional prototype of the CMM or micro-probing system as disclosed in the present invention, and (b) an enlarged view of the prototype of a wire-based probe that is attached to a stylus.

A platform stage 4 consisting of a custom built precision-motion system (from Alio Industries) with three linear stages having less than 100 nm resolution, and a spindle (NSK E800Z) at maximum 80,000 rev/min (RPM) were used to test the functional prototype of the wire-based probing system (FIG. 14a). A Mitutoyo gauge block (ASME grade 0) was used as test piece, and the contact between the wire-based probe 1 and the gauge surface was measured using the AE detection or sensing method described above. A prototype of wire-based probe 1 was fabricated as shown in FIG. 14b. Physical Acoustics Nano 30 was used as AE sensor 6 for the detection of the touch between the probe tip and the block gauge surface. In order to measure the contact force, a Kistler MiniDyn 9256C1 dynamometer was used as shown in FIG. 14a.

AE and Force Sensing Analysis

Experiments were conducted to examine the AE and force signals during the contact between the wire-based probe tip and the gauge surface. FIG. 15 shows measured profiles of the AE and force signals at the spindle speed of 60,000 rpm and the approaching speed of 3 mm/min, resulting in the feed rate of 0.05 μm/rev. As soon as the touch is detected, the probe was stopped for two seconds and retracted back from the surface.

During the two seconds that the probe was stationary, the wire or probe tip kept touching the surface per revolution.

Figure 15A:
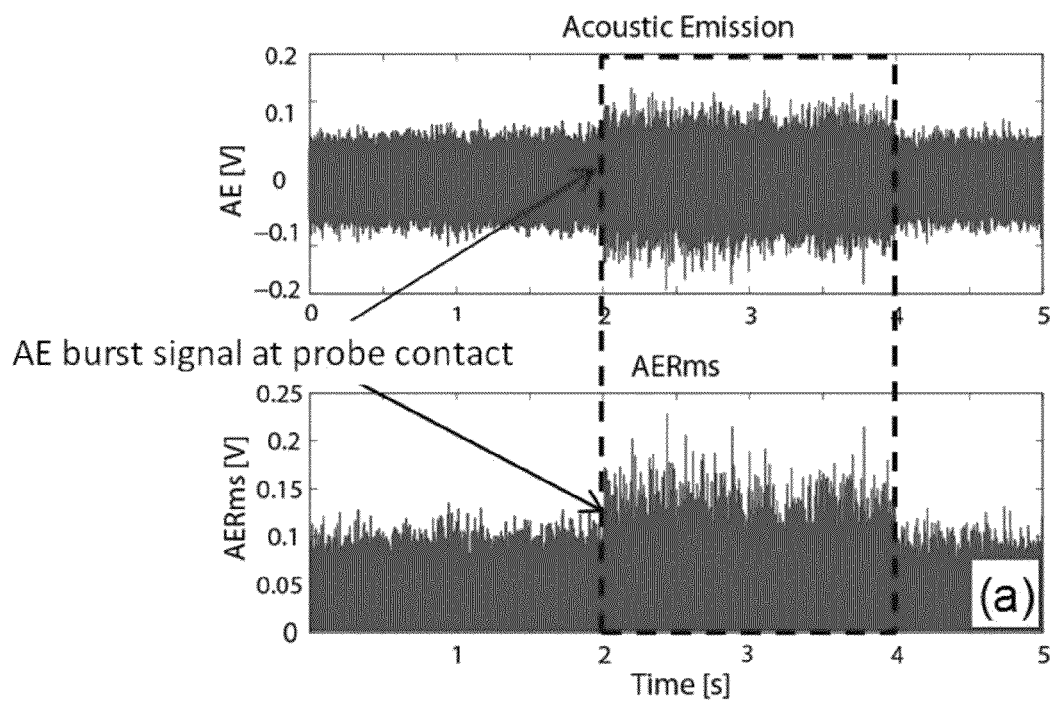
FIG. 15A provides graphical examples of AE signal profile at the event of physical contact between the rotating wire-based probe and the surface of an object, while FIG. 15B provides graphical examples of force signals in X, Y and Z directions at the event of physical contact between the rotating wire-based probe and the surface of an object.
Figure 15B:
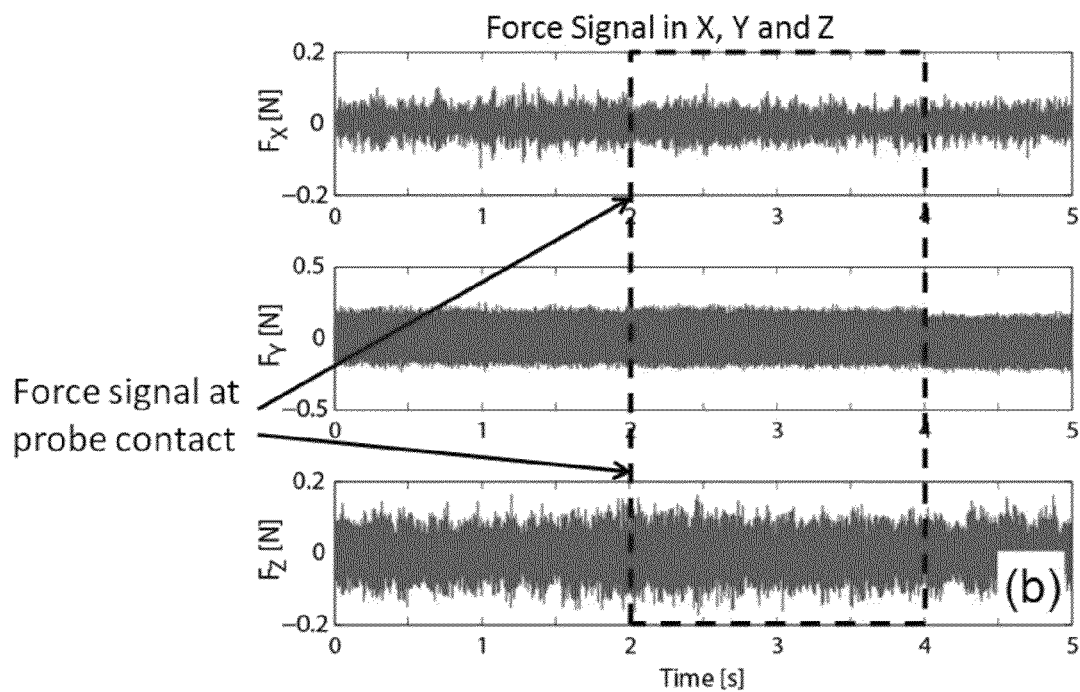
Figure 16:
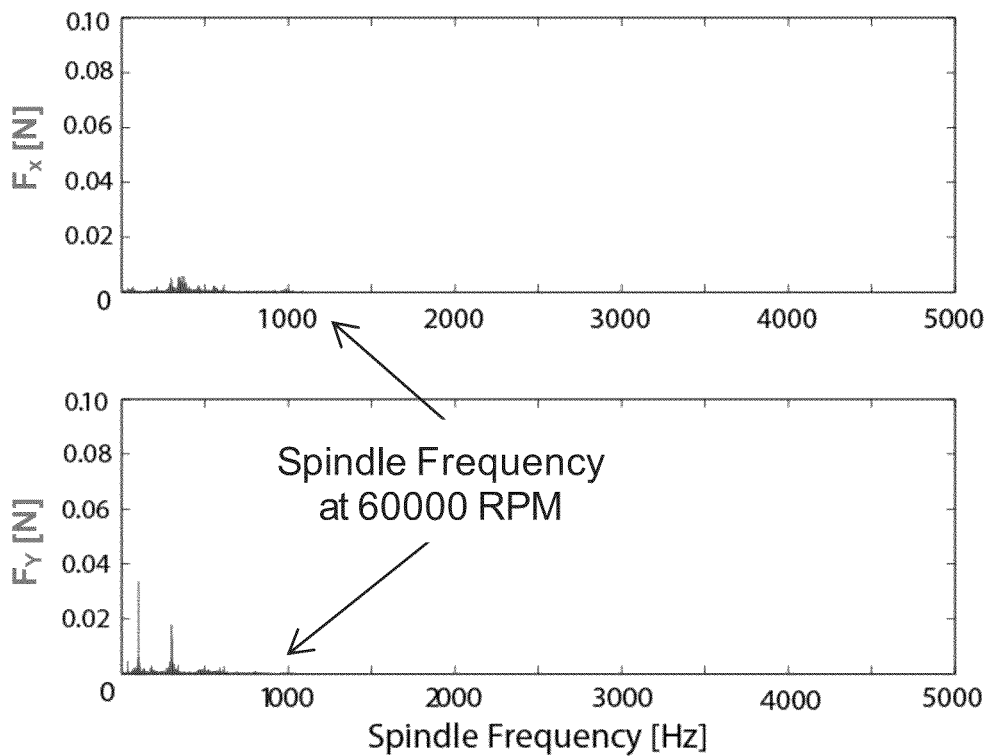
FIG. 16 provides graphical illustrations of frequency spectra of force signals in X and Y directions.

As shown in FIG. 15*a* between 2 and 4 seconds, increase in the AE amplitudes as well as in the root mean square value of the AE signals (AERms) is clearly seen. However, the force signals in all X, Y, and Z directions shown in FIG. 15*b* do not show much increase in the magnitudes. The frequency spectra of the force signals shown in FIG. 16 reveal that there is no peak at the spindle frequency (1000 Hz), but there seem to be noise signals at frequencies lower than 500 Hz. This indicates that the magnitudes of the contact forces were lower than those of the noise signals. This also shows that the AE signals are sensitive and effective for contact detection using the wire-based probe.

Figure 17:
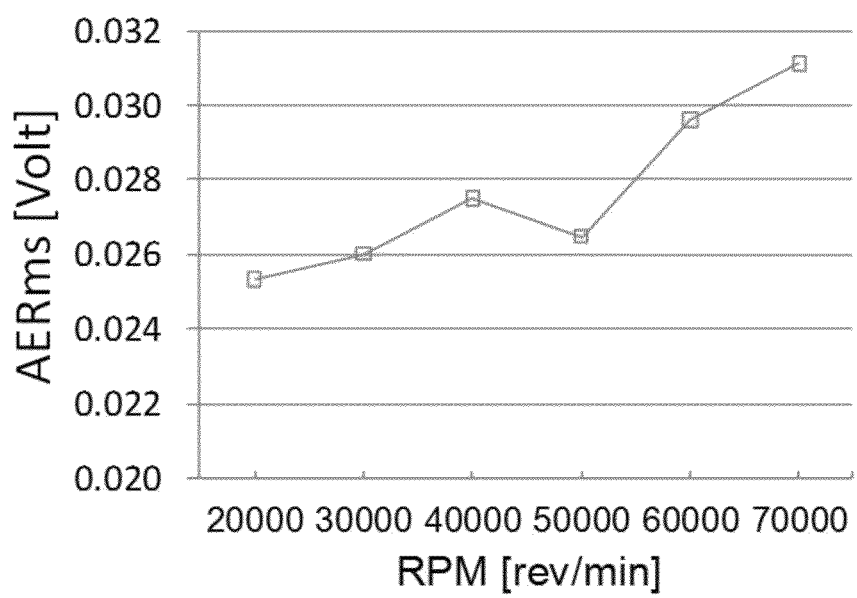
FIG. 17 is a graphical illustration showing the effect of the RPM of wire-based probe (or spindle speed) on the root mean square value of the AE signals (AERms).

FIG. 17 shows how the AERms values depend on the RPM of the wire-based probe. As shown, the AERms increases almost linearly with the RPM, indicating that the signal-to-noise ratio increases with increasing RPM. More AE is generated because of the higher impact caused by the higher wire tip velocity at higher RPM. This implies that probing at higher RPM may be more desirable as long as the imbalance dynamics does not play a role in causing significant errors in the measurement. Further study on the probe tip dynamics will enhance understanding of an optimum RPM for probing.

Repeatability Experiments

Experiments were conducted to examine the repeatability of the wire-based probing system. Experiments were also conducted to verify the effectiveness of the wire-based probe with respect to the probe approaching speed, spindle speed (RPM), probe bend angle, and wire length. The probing measurements were carried out using the wire-based probing system. Two experimental results under an identical condition are conducted and, which is separately plotted into Exp. #1 and Exp. #2 in the Figures. The each touch operation was repeated ten times and the repeatability is expressed into three-sigma (3σ) as an evaluation indicator. Parameters such as spindle speed, approaching speed, and probe geometries such as wire length and bend angle seem to affect the repeatability of the wire-based probing system. Thus, the effect of each parameter on the probing system repeatability was studied and verified.

Effect of Spindle Speed

Figure 18:
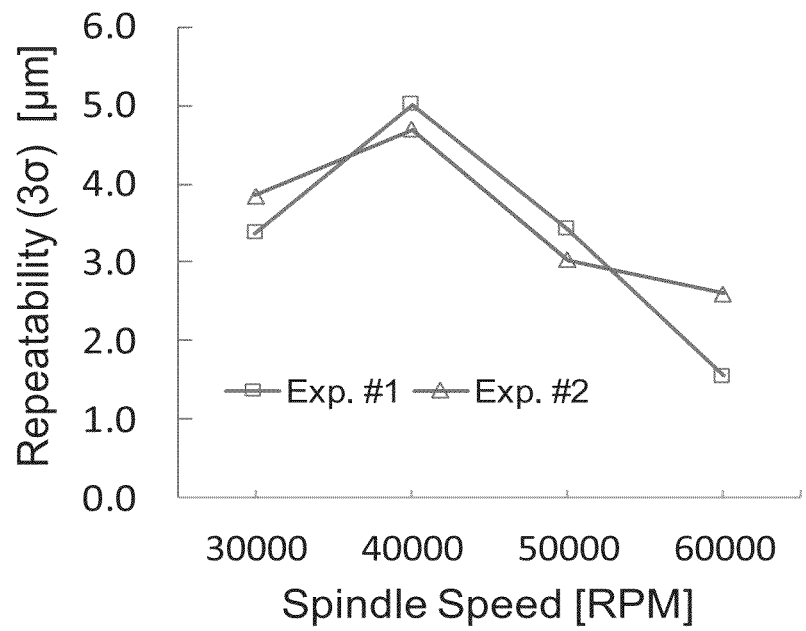
FIG. 18 is a graphical illustration showing the effect of spindle speed on repeatability.

To study the effect of the spindle speed, four different speeds from 30,000 to 60,000 rev/min (RPM) were selected at the approaching speed of 0.6 mm/min, wire length of 1.0 mm, and bend angle of 30 degrees. The effect of spindle speed on AERms was given in FIG. 17, which showed that increasing spindle speed increased AERms. Similar results for the effect on repeatability are shown in FIG. 18. As the spindle speed is increased, the repeatability seems to improve as well due to the increased sensitivity, except at 30,000 rpm. The decrease in the effect of the spindle dynamics at 30,000 rpm may have improved the repeatability of the probing system. Further study is required to examine the effect of the spindle dynamics. At 60,000 rpm, the system's repeatability is within 1.5 to 2.5 µm.

Effect of Approaching Speed

Figure 19:
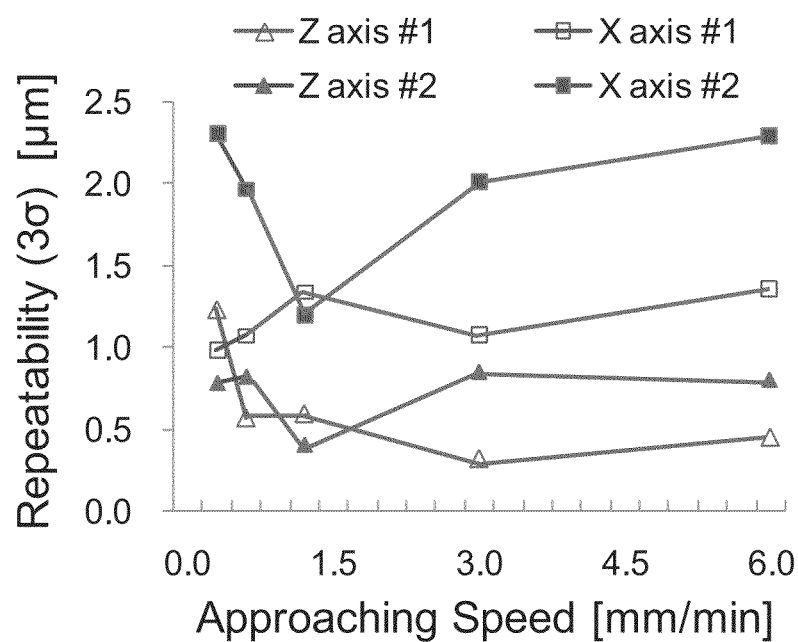
FIG. 19 is a graphical illustration showing the effect of approaching speed of the probe on repeatability.

As shown in FIG. 19, better repeatability is achieved in the Z direction than in the X direction at the spindle speed of 50000 rpm. This may be due to longer touch between the probe tip and the surface in the Z direction. Also, as shown in FIG. 19, the approaching speed does not seem to have significant effect on the repeatability although the resolution is increases with the approaching speed. This is because, for the approaching speeds considered, the resolution (~0.1 µm) is much smaller than the repeatability values. The noise in the signal, spindle dynamics, and wire vibrations may have caused the repeatability values to be much higher than the resolution. Further study is required to understand the factors affecting the repeatability and reduce the effects of these factors to improve the repeatability.

Effect of Wire Geometry

Figure 20A:
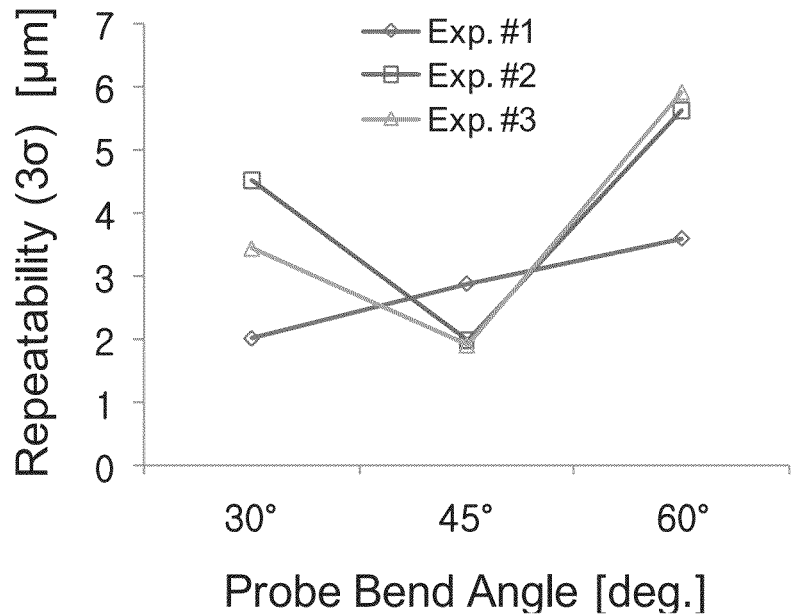
Figure 20B:
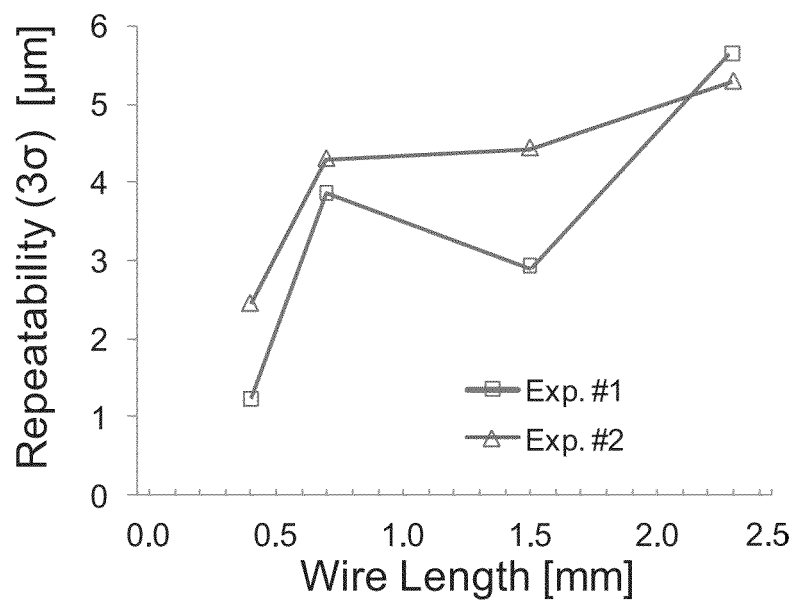
FIG. 20B is a graphical illustration showing the effect of the probe wire length on repeatability.

The effects of the wire geometry (wire bend angle and length) are also examined. Repeatability experiments were conducted using three different bend angles (30, 45, and 60 degrees) with 1 mm wire length probe and four different wire lengths (0.5, 0.8, 1.6, and 2.4 mm) with 30 degree bend angle. The spindle speed and the approaching speed were 60,000 rpm and 0.6 mm/min, respectively. The results are shown in FIG. 20. The bend angle of 45° seems to result in the best repeatability values as shown in FIG. 20*a*. For the wire length as shown in FIG. 20*b*, as the length increases, the repeatability increases. This may be due to increased flexibility of the wire as the length is increased. Consequently, shorter wire length is preferred for better repeatability of the wire-based probe.

Various experiments have been conducted to investigate the effect of certain factors that can affect the performance of the disclosed apparatus and methods. The results of those experiments demonstrate the following:

(a) AE signals generated by the physical contact between the rotating wire-based probe and the surface of an object provide a sensitive and effective method for detecting or probing the said surface of an object.

(b) Sensing in all axial directions (X, Y and Z) is possible with at least one AE sensor that is attached to the platform stage of the CMM or probing system of the present invention.

(c) The CMM or probing system has better repeatability in the Z direction possibly due to longer contact per revolution.

(d) The sensitivity and repeatability of the CMM or probing system are better with higher spindle speed and longer wire length for the probe.

(e) Repeatability of less than one micron was achieved by the proposed CMM or probing system, thereby making it an effective tool for conducting measurements in the micro-scale.

(f) The approaching speed does not have significant effect on the probing system repeatability.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An apparatus for measuring dimensions of a micro-scale object, comprising:
   a movable stylus positionable to contact an object to be measured;
   a probe rotatably coupled to the stylus, the probe having a distal end that circumscribes a circle when rotated;
   at least one acoustic emissions sensor operatively coupled to the probe;
   wherein the sensor is operative to detect acoustic emissions generated from contact between the distal end of the probe and the object, thereby allowing dimensions of the object to be determined.

2. The apparatus of claim 1, wherein the probe comprises an angled element that is angled with respect to an axis of rotation extending through a proximal end of the probe where the probe is joined to the stylus.

3. The apparatus of claim 2, wherein the probe's path in rotation defines a cone shape.

4. The apparatus of claim 1, further comprising a platform upon which the object can be positioned, and wherein the acoustic emissions sensor is connected to the platform.

5. The apparatus of claim 1, wherein the apparatus comprises a circuit that includes the acoustic emissions sensor and a processor, the processor being operable to process the acoustic emissions data received from the acoustic emissions sensor and to subject the acoustic emissions data to an algorithm to determine coordinates in space at points of contact along the object.

6. The apparatus of claim 5, further comprising a display operable to display data to a user during operation of the apparatus.

7. The apparatus of claim 1, wherein the probe comprises a bent wire.

8. The apparatus of claim 1, wherein the probe comprises an angled element having a proximal end positioned at an axis of rotation and a distal end spaced apart from the axis of rotation.

9. The apparatus of claim 8, wherein an angle between the axis of rotation and the angled element is between about 30 degrees and about 60 degrees.

10. The apparatus of claim 8, wherein the probe has a length of at least 1 mm.

11. A method of measuring dimensions of a micro-scale object, comprising:
    positioning a movable probe near an object to be measured;
    causing a distal end of the probe to rotate;
    detecting acoustic emissions; and
    if detected acoustic emissions indicate that the distal end of the probe is in contact with the object, then pausing movement of the probe and determining a coordinate corresponding to the contact between the probe and the object.

12. The method of claim 11, further comprising determining if the detected acoustic emissions exceed a threshold, and if not, then continuing rotation of the probe without pausing.

13. The method of claim 11, wherein detecting acoustic emissions includes detecting acoustic emissions with an acoustic emissions sensor operatively coupled to the probe.

14. The method of claim 11, causing a distal end of the probe to rotate includes causing rotation at about 30,000 rpm to about 60,000 rpm.

15. The method of claim 11, wherein causing the distal end of the probe to rotate comprises moving the distal end of the probe to circumscribe a circle of about 200 µm to about 700 µm.

16. The method of claim 11, further comprising resuming rotation of the probe following determination of the coordinate.

17. The method of claim 11, further comprising using a computing device programmed with different algorithms for determining a coordinate depending upon the probe's direction of approach toward the object.

18. The method of claim 11, wherein the probe is caused to contact the object at multiple contact points, further comprising determining a profile of the object from the multiple contact points.

19. The method of claim 11, further comprising setting an approach speed of the probe towards the object to increase accuracy.

20. The method of claim 11, further comprising setting a probing force that the probe exerts upon contact with the object to increase accuracy.

* * * * *